United States Patent
Akers et al.

(10) Patent No.: US 7,899,686 B1
(45) Date of Patent: Mar. 1, 2011

(54) SYSTEM AND METHOD FOR MANAGING PRESCRIPTION DATA

(75) Inventors: William Rex Akers, Colleyville, TX (US); Craig Alan Walker, Austin, TX (US); Michael T. Rupp, Glendale, AZ (US); Gregory B. Ehrhardt, Fort Worth, TX (US); Christian T. Ehrhardt, Fort Worth, TX (US); Brian M. Hudson, Irving, TX (US); Matthew M. Bergmann, Franklin, TN (US)

(73) Assignee: William Rex Akers, Fort Worth, TX (US)

( * ) Notice: Subject to any disclaimer, the term of this patent is extended or adjusted under 35 U.S.C. 154(b) by 393 days.

(21) Appl. No.: 10/371,593

(22) Filed: Feb. 21, 2003

(51) Int. Cl.
*G06F 19/00* (2006.01)

(52) U.S. Cl. .................... 705/3; 705/2; 705/4; 600/300

(58) Field of Classification Search .............. 705/7, 705/14, 20, 28, 402, 2, 3, 4
See application file for complete search history.

(56) References Cited

U.S. PATENT DOCUMENTS

| | | | |
|---|---|---|---|
| 5,704,044 A | 12/1997 | Tarter et al. | |
| 5,911,132 A * | 6/1999 | Sloane | 705/3 |
| 6,343,271 B1 * | 1/2002 | Peterson et al. | 705/4 |
| 6,654,724 B1 * | 11/2003 | Rubin et al. | 705/3 |
| 6,687,676 B1 * | 2/2004 | Denny | 705/2 |
| 2001/0037216 A1 * | 11/2001 | Oscar et al. | 705/2 |
| 2001/0047299 A1 * | 11/2001 | Brewer et al. | 705/14 |
| 2002/0002495 A1 * | 1/2002 | Ullman | 705/21 |
| 2002/0077867 A1 * | 6/2002 | Gittins et al. | 705/4 |
| 2002/0107641 A1 * | 8/2002 | Schaeffer et al. | 702/19 |
| 2002/0165736 A1 * | 11/2002 | Tolle et al. | 705/3 |
| 2003/0055687 A1 * | 3/2003 | Rudy | 705/4 |
| 2003/0055809 A1 | 3/2003 | Bhat | |
| 2003/0149625 A1 * | 8/2003 | Leonardi et al. | 705/14 |
| 2003/0187615 A1 * | 10/2003 | Epler et al. | 702/181 |
| 2003/0236697 A1 * | 12/2003 | Rupp | 705/10 |
| 2004/0039599 A1 * | 2/2004 | Fralic | 705/2 |
| 2004/0054685 A1 | 3/2004 | Rahn et al. | |
| 2004/0117323 A1 * | 6/2004 | Mindala | 705/400 |
| 2004/0148195 A1 | 7/2004 | Kalies | |
| 2004/0148196 A1 * | 7/2004 | Kalies | 705/2 |
| 2004/0225528 A1 | 11/2004 | Brock | |
| 2005/0065824 A1 | 3/2005 | Kohan | |

(Continued)

OTHER PUBLICATIONS

Sage, Richard; Affidavit with Exhibits, Jul. 25, 2007.

(Continued)

*Primary Examiner*—R. D Rines
(74) *Attorney, Agent, or Firm*—Carr LLP

(57) ABSTRACT

A system for managing prescription data is provided. The system includes a switch system receiving prescription data from a pharmacy, such as medicine identification data, dosage data, number of doses data, fill date data, and number of refills data. A data volume sales system generates volume sales data from the prescription data, such as the percentage of a given type of medicine sold for a manufacturer relative to all manufacturers for that medicine. A data volume rebate by unit system receives the prescription data and, the volume sales data and generates incentive target reward data, such as the number of additional units of medicine that must be sold to reach a predetermined sales volume associated with a rebate level.

20 Claims, 6 Drawing Sheets

U.S. PATENT DOCUMENTS

2005/0080651 A1 4/2005 Morrison et al.

OTHER PUBLICATIONS

International Search Report of PCT/US2006/012425, Aug. 16, 2007, ISA/US.

U.S. Appl. No. 11/098,168; Office Action; Jul. 8, 2009.
U.S. Appl. No. 11/098,168; Response with Petition to Revive; Apr. 8, 2010.

* cited by examiner

100

200

300

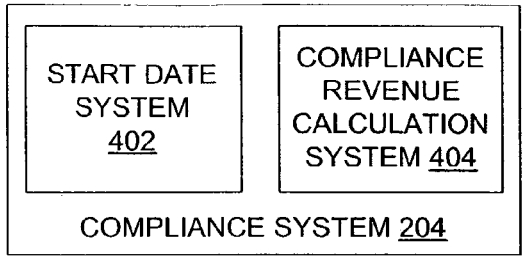
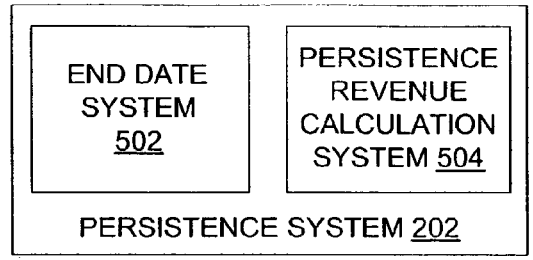
⇧400  FIGURE 4
⇧500  FIGURE 5
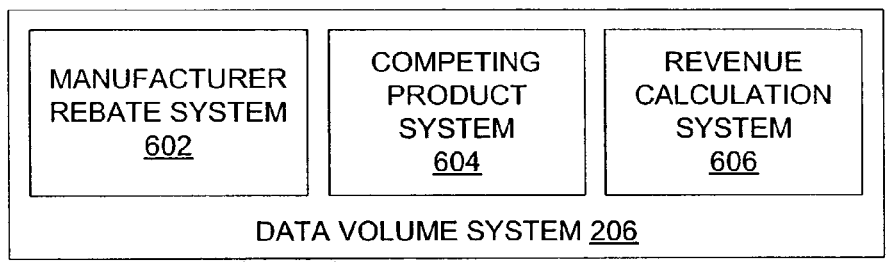
⇧600  FIGURE 6
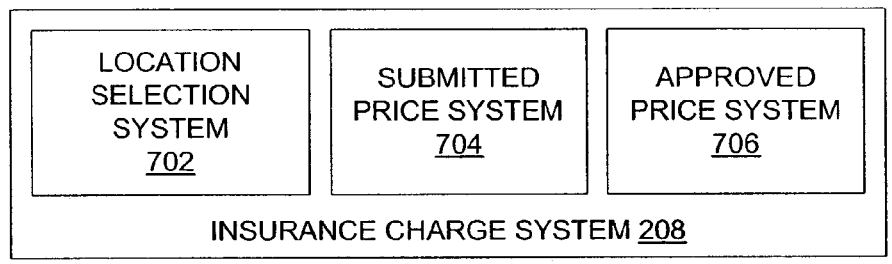
⇧700  FIGURE 7

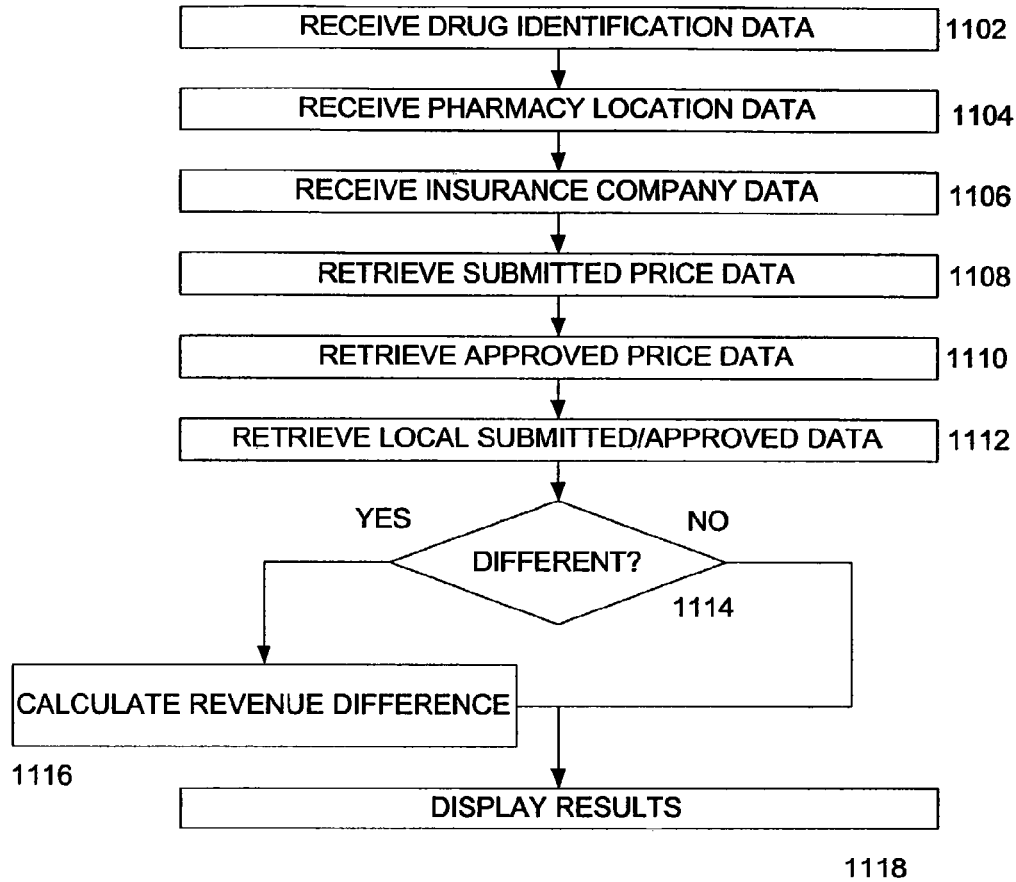
↑1100  FIGURE 11
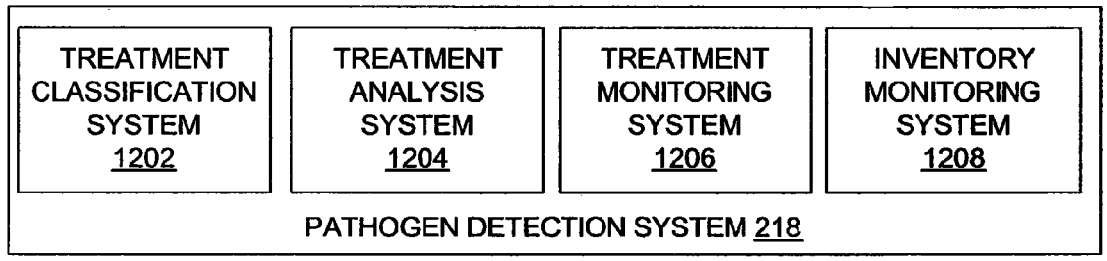
↑1200  FIGURE 12

US 7,899,686 B1

SYSTEM AND METHOD FOR MANAGING PRESCRIPTION DATA

FIELD OF THE INVENTION

The present invention pertains to prescription data processing, and more specifically to a system and method for prescription data processing that allow data of interest to pharmacies and manufacturers to be identified and provided.

BACKGROUND OF THE INVENTION

Systems for processing prescription data are known in the art. These systems include prescription authorization switches that are used to submit prescription data to insurance companies for approval of charges. The pharmacy will typically submit the prescription data to the insurance company with a submitted price, and the insurance company will then respond with an indication of whether the charge is approved, approved with a different price, or denied, such as where the insurance policy is not active. The pharmacist can then dispense the prescription and assess charges to the customer based on the response from the insurance company.

Although such switch systems process prescription data, no data management functionality is provided. For example, a manufacturer rebate program implemented in conjunction with prior art switch systems did not provide feedback to pharmacists during the period that the rebate marketing program was active. Thus, although pharmacists received an incentive for selling a predetermined volume of product, they were not receiving information that alerted them as to the additional amount of product that had to be sold to reach a bonus or rebate level. As a result, the incentive programs resulted in incentive payments to pharmacists but were not creating an incentive for the pharmacist to sell more of a given product.

SUMMARY OF THE INVENTION

In accordance with the present invention, a system and method for managing prescription data are provided that overcome known problems with managing prescription data.

In particular, a system and method for managing prescription data are provided that allow prescription data to be used to optimize pharmacy and manufacturer operations.

In accordance with an exemplary embodiment of the present invention, a system for managing prescription data is provided. The system includes a switch system receiving prescription data from a pharmacy, such as medicine identification data, dosage data, number of doses data, fill date data, and number of refills data. A data volume system generates volume data from the prescription data, such as the volume of a given type of medicine sold for a manufacturer, as well as data for all manufacturers of that medicine. A data volume rebate by unit system receives the prescription data and the sales volume data and generates data volume rebate by unit data, such as the number of additional units of medicine that must be sold to reach a predetermined volume associated with a volume rebate.

The present invention provides many important technical advantages. One important technical advantage of the present invention is a system and method for managing prescription data that allows manufacturers to implement volume rebate plans and that allows pharmacists to obtain market price information for use in submitting claims for payment by insurance companies.

Those skilled in the art will further appreciate the advantages and superior features of the invention together with other important aspects thereof on reading the detailed description that follows in conjunction with the drawings.

BRIEF DESCRIPTION OF THE SEVERAL VIEWS OF THE DRAWINGS

FIG. 4 is a diagram of a system for providing compliance data in accordance with an exemplary embodiment of the present invention;

FIG. 5 is a diagram of a system for providing persistence data in accordance with an exemplary embodiment of the present invention;

FIG. 6 is a diagram of a system for generating volume data in accordance with an exemplary embodiment of the present invention;

FIG. 7 is a diagram of a system for providing insurance charge functionality in accordance with an exemplary embodiment in the present invention;

FIG. 11 is a flowchart of method for determining reasonable and customary charges for pharmaceuticals in accordance with an exemplary embodiment of the present invention;

FIG. 12 is a diagram of a system for detecting pathogens that have been released into a population based on changes in pharmaceutical use levels in accordance with an exemplary embodiment of the present invention.

DETAILED DESCRIPTION OF THE INVENTION

Figure 1:
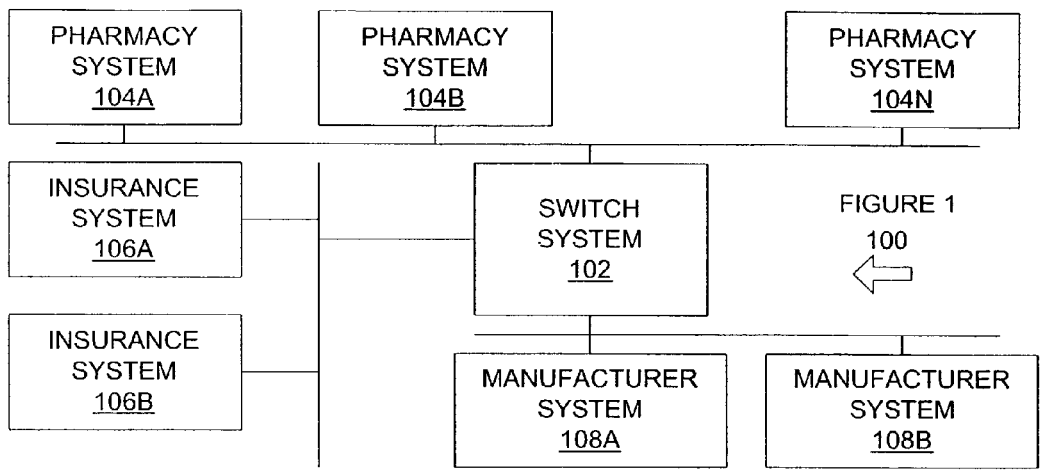
FIG. 1 is a diagram of a system for managing prescription data in accordance with exemplary embodiment of the present invention.

In the description that follows like parts are marked throughout the specification and drawings with the same reference numerals, respectively. The drawing figures are not necessarily to scale and certain features may be shown in somewhat generalized or schematic form in the interest of clarity and conciseness.

FIG. 1 is a diagram of a system 100 for managing prescription data in accordance with exemplary embodiment of the present invention. System 100 allows prescription data to be managed to facilitate the use of that data by pharmacies and pharmaceutical manufacturers.

System 100 includes switch system 102, which can be implemented in hardware, software, or a suitable combination of hardware and software, and which can be one or more software systems operating on a general purpose server platform. As used herein, a hardware system can include discrete semiconductor devices, an application-specific integrated circuit, a field programmable gate array or other suitable devices. A software system can include one or more objects, agents, threads, lines of code, subroutines, separate software applications, user-readable (source) code, machine-readable (object) code, two or more lines of code in two or more corresponding software applications, databases, or other suitable software architectures. In one exemplary embodiment, a software system can include one or more lines of code in a general purpose software application, such as an operating system, and one or more lines of code in a specific purpose software application.

Switch system 102 is coupled to pharmacy systems 104a through 104n, each of which can be implemented in hardware, software, or a suitable combination of hardware and software, and which can be one or more software systems operating on a general purpose computing platform. As used herein, the term "couple" and its cognate terms, such as "couples" and "coupled," can include a physical connection (such as a copper conductor), a virtual connection (such as through randomly assigned memory locations of a data memory device), a logical connection (such as through logical gates of a semiconducting device), other suitable connections, or a suitable combination of such connections. In one exemplary embodiment, systems and components are coupled to other systems and components through intervening systems and components, such as through an operating system.

Pharmacy systems 104a through 104n provide prescription data to switch system 102 in order to obtain approval for payment of the prescription under one or more insurance providers. Switch system 102 is also coupled to insurance systems 106a and 106b, each of which can be implemented in hardware, software, or a suitable combination of hardware and software, and which can be one or more software systems operating on a general purpose processing platform. The prescription data received from pharmacy systems 104a through 104n at switch system 102 is transmitted to insurance system 106a, insurance system 106b, or other suitable insurance systems. Insurance systems 106a and 106b process the prescription data, such as to authorize or reject a claim for payment, to provide an amount for which a claim will be paid, or to provide other suitable data. The data is then transmitted back to switch system 102, which forwards the payment data to the pharmacy system 104a through 104n that submitted to the prescription data. In this manner, each pharmacy system 104a through 104n can receive approval for payment of a prescription under a patient's insurance policy prior to completing the sale of the prescription to the patient.

In addition, switch system 102 interfaces with manufacturer system 108a, manufacturer system 108b, and other suitable manufacturer systems. Manufacturer systems 108a and 108b can provide volume rebate program data to switch system 102 for use with pharmacy systems 104a through 104n. In one exemplary embodiment, manufacturer systems 108a and 108b provide volume rebate data for pharmacists to use generic or multi-sourced pharmaceuticals available from manufacturer systems 108a and 108b. In this exemplary embodiment, manufacturer system 108a can create a rebate program for a first pharmaceutical "X" for which manufacturer system 108b also manufactures a competing product "Y" that contains the same active ingredient. In order to maintain its volume rebate per unit of the pharmaceutical, manufacturer system 108a can offer pharmacy systems 104a through 104n a predetermined discount or bonus for selling a predetermined volume of "X."

For example, if pharmacy system 104a sells 100 units of "X" and "Y," then manufacturer system 108a can provide a bonus or rebate level for sales of "X" for which volume meets or exceeds a predetermined unit total, such as 50% of all units sold, 80% of all units sold, or other suitable levels. Likewise, one or more additional bonus levels can be provided, such as to create an increasing rebate for additional sales after the first bonus level has been met. Pharmacy system 104a and pharmacy system 104b can also receive different bonus levels for the same data volume rebate by unit totals, based on location, the market in that location, demographic factors, relationships with physicians, and other suitable factors. For example, pharmacy system 104a could receive a bonus for a data volume level of 60%, whereas pharmacy 104b could receive the same bonus for a data volume level of 80%, such as where the manufacturer has a good reputation with the prescribing physicians in the area around the pharmacy. In this manner, manufacturers can use system 100 to optimize their rebate program based on existing data volume.

Likewise, switch system 102 can provide pharmaceutical sales data to manufacturer systems 108a and 108b. In one exemplary embodiment, the operator of manufacturer system 108a may want data to define its rebate program in one or more demographic areas, for one or more demographic groups, or for other suitable purposes. Switch system 102 can extract data submitted by pharmacy systems 104a through 104n to insurance systems 106a and 106b, and can provide the data to manufacturer systems 108a and 108b after removing patient-specific data. In this exemplary embodiment, switch system 102 can provide data to manufacturer systems 108a and 108b regarding the sex of the patient, the age of the patient, the insurance company of the patient, the doctor the patient has seen, or other suitable data.

Pharmacy systems 104a through 104n can also request data from switch system 102. In one exemplary embodiment, the data requested can include data regarding approved insurance charges for pharmaceuticals submitted to insurance systems 106a and 106b. In this exemplary embodiment, each of pharmacy systems 104a through 104n can submit requests for approval of expenses to insurance systems 106a and 106b. These requests include an estimate of the market value for the pharmaceuticals provided to a patient in response to the prescription for which a claim is submitted. Because such prices are not advertised, estimation of the market value for a pharmaceutical is difficult. Insurance system 106a can approve a request from pharmacy system 104a for payment of a claim at a first estimated value, and can approve a request from pharmacy system 104b for payment of the same claim at a higher estimated value. In this exemplary embodiment, pharmacy system 104a can request data from switch system 102 regarding payments made on claims to other pharmacy by insurance systems 106a and 106b. In this manner, pharmacy system 104a can increase its estimated values for submission to insurance systems 106a and 106b based on what other pharmacy systems in its local market have been estimating the value to be, and what the insurance companies have been approving.

In addition, pharmacy systems 104a through 104n can request data from switch system 102 regarding rebate levels for rebates through manufacturer systems 108a and 108b, profit and loss data, and other suitable data. Switch system 102 can provide this data to pharmacy systems on a per item basis, can process data pertaining to volume rebate programs based on a percentage of the cost saved for each of the pharmacy systems 104a through 104n, can manage data for manufacturer systems based on the number of units represented by that data, and can perform other suitable functions.

In operation, system 100 allows pharmacy systems and manufacturer systems to receive data from a switch system 102 to optimize the performance of pharmacy systems and manufacturer systems. In one exemplary embodiment, pharmacy systems can receive data regarding what other pharmacy systems have been approved for reimbursement submitted for particular pharmaceuticals, based on the number of units of pharmaceutical in the package, dosage, and the insurance plan under which the claim was submitted. In this manner, a pharmacy system can maximize its estimated value for product when other reliable indicators for the product are unavailable.

In another exemplary embodiment, pharmacy systems 104a through 104n can receive rebate data from manufacturer systems 108a and 108b, and can determine the number of units they must sell within a timeframe in order to reach the bonus levels. In another exemplary embodiment, manufacturer systems 108a and 108b can receive data regarding other similar drugs sold by the manufacturers that have been dispensed by pharmacists at pharmacy systems 104a through 104n, such as to determine sales volume, demographic sales data, and other data that can be used to optimize rebate plans, volume rebates, or other factors.

Figure 2:
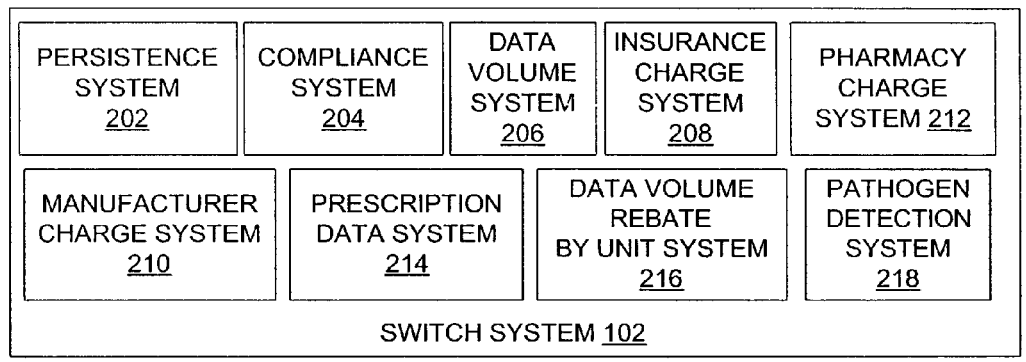
FIG. 2 is a diagram of system for switching prescription data to insurance companies and manufacturers in accordance with an exemplary embodiment of the present invention.

FIG. 2 is a diagram of system 200 for switching prescription data to insurance companies and manufacturers in accordance with an exemplary embodiment of the present invention. System 200 allows prescription data from pharmacies to be submitted to insurers for approval of payments, and provides other useful functionality.

System 200 includes switch system 102 and persistence system 202, compliance system 204, volume rebate system 206, insurance charge system 208, manufacturer charge system 210, pharmacy charge system 212, prescription data system 214, data volume rebate by unit system 216, and pathogen detection system 218, each of which can be implemented in hardware, software, or a suitable combination of hardware and software, which can be one of more software systems operating on a general purpose processing platform. Persistence system 202 provides information regarding patients having prescriptions that are going to require a refill in the future. In one exemplary embodiment, persistence system 202 can receive prescription data such as fill date data, number of dosages data, refill data, and dose frequency data, and can determine the number of days for which the prescription is good for. Persistence system 202 can then determine the date on which the prescription should require refilling, and can generate notification data for a user. In one exemplary embodiment, the notification data can include value data for filling the prescription, such as the value under a sales volume program, the value from the sale of the refill, or other suitable value data. Persistence system 202 allows a pharmacist to identify patients that will require a prescription to be refilled within a timeframe so as to allow the pharmacist to contact the patients and suggest that they refill their prescription, to ensure that the patients are using the prescription medicine, or take other suitable actions.

Compliance system 204 generates compliance data that indicates the number of days past a date on which a patient should have refilled a prescription. Compliance data is important, because it indicates that a patient is not taking a prescription and may be at risk for health problems for failing to do so. In one exemplary embodiment, compliance system 204 can receive prescription data such as date filled data, the number of dosages data, refill data, and dose frequency data, and can determine the date on which the prescription should have been refilled. Compliance system 204 can also rank out of compliance prescriptions based on the number of days out of compliance, the value of refilling the prescription to the pharmacist based on a volume rebate program or the value from the sale of the refill, or other suitable data.

Data volume system 206 is a sales volume system that generates volume data for sales of a prescription or brand of pharmaceutical. In one exemplary embodiment, data volume system 206 receives classification data and groups manufacturer's products based on active ingredients, compatibility of use (such as different drugs that can be prescribed for the same condition), compatibility of ingredients, or other suitable factors. Data volume system 206 can also determine the volume of each manufacturer's product in relation to other identical products, other compatible uses, other compatible ingredients, or other suitable data. In one exemplary embodiment, two or more manufacturers can/manufacture a prescription drug having the same active ingredient, where data volume system 206 can track the number of units sold for each manufacturer and can generate volume data for a pharmacist, a group of pharmacists, a city, or other suitable demographic groups.

Insurance charge system 208 compiles charges submitted to and paid by insurance companies for pharmaceuticals or other products. In one exemplary embodiment, insurance charge system 208 can track the submitted value and paid value for pharmaceuticals by pharmacists based on location, insurance plan, or other factors, and can provide data to pharmacists based on what insurance companies have paid for pharmaceuticals or other products based on estimates of the reasonable value of the pharmaceuticals. Insurance charge system 208 can also generate notification data, such as when a pharmacist is has entered a submitted value that is lower than the maximum paid values for a given pharmaceutical and insurance company, can generate report data showing the difference between what the pharmacist would have received if the submitted value entered by the pharmacist had been used and the amounts received using the submitted value from insurance charge system 208, can edit the submitted value data received from the pharmacist to replace the submitted value with the maximum value paid by the insurance company, and can perform other suitable functions.

Manufacturer charge system 210 tracks manufacturer charge data for managing pharmaceutical data for manufacturer. In one, exemplary embodiment, a manufacturer system 108a and 108b can provide prescription data from other sources to switch system 102 for management, such as to process to determine volume rebates, demographic data such as effectiveness of visits by sales persons, advertising campaigns, or other suitable data. In this exemplary embodiment, manufacturer charge system 210 can assess charges based on each unit for which data is being managed, based on a percentage of a cost savings to the manufacturer system, or other based on suitable factors.

Pharmacy charge system 212 tracks charges to pharmacy systems 104a through 104n for participation in sales volume programs, receipt of data, processing of insurance authorization requests by switch system 102, and other suitable processes. In one exemplary embodiment, the operator of switch system 102 can receive a percentage of the amount of money saved by each pharmacy system 104a through 104n for participation in the volume rebate program as payment for use by the pharmacy systems 104a through 104n of switch system 102. In another exemplary embodiment, pharmacy systems can be billed based on the number of transactions submitted, the amount of savings realized for use of approved insurance amount data received from switch system 102, or other suitable factors.

Prescription data system 214 stores prescription data processed by switch system 102 from pharmacy systems 104*a* through 104*n*. In one exemplary embodiment, pharmacy systems 104*a* through 104*n* can submit pharmaceutical prescription data to switch system 102 for approval by insurance systems 106A and 106B. Prescription data system 214 extracts predetermined, patient-obscured data from the submitted prescription data, such as data pertaining to the type of medicine, the product number, the manufacturer, the number of units, the dosage of each unit, the price of each unit, the doctor's office that prescribed the units, the zip code or other location data for the person receiving the units or where the drug store is, the age of the patient, the sex of the patient, or other suitable data. Prescription data system 214 strips all patient-specific information so that the resulting data can be used for volume rebate analysis, demographic analysis, provision to other pharmacy systems, other manufacturer systems, or other suitable systems.

Data volume rebate by unit system 216 is a rebate system that determines the profit or loss for handling a specific prescription. In one exemplary embodiment, data volume rebate by unit system 216 can prompt an operator or pharmacy system to enter the percentage that represents an acquisition cost using the average wholesale prices of basis of cost for a drug. For example, the acquisition cost as a percentage of the average wholesale price for a drug that is protected by a patent and available from a single source may be much lower than the percentage of the total cost for generically available drugs. Data volume rebate by unit system 216 tracks the acquisition cost data or estimates for a prescription that are provided by a pharmacist, and the amounts paid for the prescription by insurance companies, patient co-pays, and other payments, in order to determine the individual sale profit or loss for that prescription. Data volume rebate by unit system 216 can track the number of units that have been sold or that need to be sold in order to comply with a rebate level from a manufacturer, and can also generate data regarding the revenue that has been earned or the potential value from selling the additional units. The data volume rebate by unit system can also be a market share system that provides increasing rebate levels based on market share if that process is permitted under law. If a market share program is not permitted, the data volume rebate by unit system allows the manufacturer to set rebate levels in light of sales data for all products that may result in the same outcome as a market share system, albeit through a different process.

Pathogen detection system 218 detects geographic incidence of pathogen introduction into a population by analyzing trend data for pharmaceuticals that would be prescribed to treat the symptoms caused by such pathogens. In one exemplary embodiment, pathogen detection system 218 can classify pharmaceuticals into categories that might be used to treat the symptoms from pathogens, such as chemical agents, biological agents, radioactive materials, or other similar materials. This classification can take into account the possibility of misdiagnosis, such as because of the difficulty of detecting the pathogen through its symptoms, the likelihood of physicians to discount the pathogen as a source because of the low possibility of its being present, or other factors. For example, exposure to certain forms of radioactive materials can result in symptoms that might not be suspected by a physician if there are no sources of radioactive contamination in the area and no reports of radioactive contamination. Nevertheless, clandestine exposure of a population to radioactive contamination could still be detected early by determining which pharmaceuticals would likely be prescribed to treat its symptoms, and then monitoring those pharmaceuticals to determine when the frequency of prescription exceeds normal variations. A similar process can likewise be used, such as for chemical toxins (e.g. ricin or nerve agents), biological agents (e.g. the plague bacilli or smallpox virus), or other pathogens. Pathogen detection system can also generate geographic trend data, such as data that indicates a direction of movement of an infectious disease, such as where the pathogen is delivered by air, a river, an aquifer, or other processes that would result in a geographic trend.

In operation, system 200 allows data received for processing of prescription charges and obtaining approval from insurance companies to be managed to identify information for use by manufacturers of pharmaceuticals, pharmacists, or other suitable entities. System 200 allows sales volume data to be used in real time to provide an incentive to pharmacists to sell manufacturer's products, allows manufacturers to obtain real time demographic data for use in determining the efficacy of advertising and sales techniques, and provides other suitable data.

Figure 3:
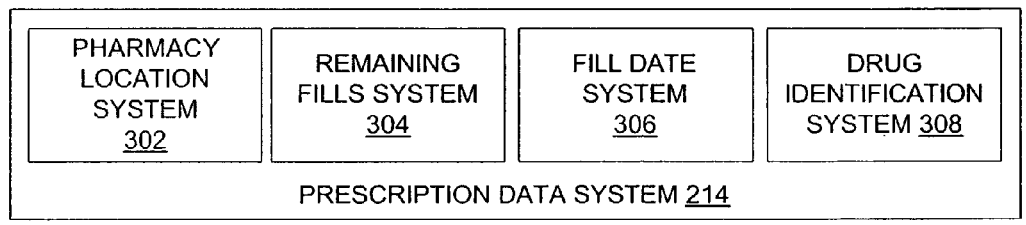
FIG. 3 is a diagram of a system for managing prescription data in accordance with an exemplary embodiment of the present invention.

FIG. 3 is a diagram of a system 300 for managing prescription data in accordance with an exemplary embodiment of the present invention. System 300 includes prescription data system 214 and pharmacy location system 302, remaining fill system 304, fill date system 306, and drug identification system 308, each of which can be implemented in hardware, software, or a suitable combination of hardware and software, and which can be one or more software systems operating on a general purpose processing platform. System 300 can retrieve data processed by switch system 102 or other suitable systems.

Pharmacy location system 302 receives pharmacy location data for use in tracking demographic data, determining pharmacies in the same market area for cost comparison data, and other suitable purposes. In one exemplary embodiment, pharmacy location system 302 can also include the number of pharmacies within a predetermined distance to a doctor's office, the number of pharmacies within a zip code or based on other location data. For example, pharmacy location system 302 can allow an insurance company or manufacturer system operator to determine the number of pharmacies within a predetermined distance to a doctor's office, such as to determine the effectiveness of a visit to the doctor by a salesman.

Remaining fill system 304 stores the number of dosages remaining for a prescription. In one exemplary embodiment, when a prescription is initially processed by pharmacy, the number of refills for the prescription can be stored, as well as the number of dosages per prescription, the dose size, and other suitable data. Remaining fill system 304 allows active prescriptions to be readily identified, such as for determining persistence or compliance information or other suitable information.

Fill date system 306 stores fill date data that is used to determine the number of days out of compliance of a prescription, the persistence data or the date on which an existing prescription will lapse, or other suitable data. Fill date system 306 can be used to generate persistence or compliance data for other suitable purposes.

Drug identification system 308 stores drug identification data, such as product identification numbers, brand names, active ingredient dosages, and other suitable data. In one exemplary embodiment, drug identification system 308 stores related drug information, such as competitor's drugs, drugs having the same treatment regime but having a different chemical compound, or other suitable data.

In operating, prescription data system 214 stores prescription data received from pharmacy systems when pharmaceuticals or prescriptions are initially filled. Prescription data system 214 is coupled to persistence system 202, compliance system 204, insurance charge system 208, manufacturer charge system 210, and pharmacy charge system 212, and volume data volume rebate by unit system 216, and provides data required by those systems to perform various functions.

FIG. 4 is a diagram of a system 400 for providing compliance data in accordance with an exemplary embodiment of the present invention. System 400 includes compliance system 204, start date system 402 and compliance revenue calculation system 404, each of which can be implemented in hardware, software, or a suitable combination of hardware and software, and which can be one or more software systems operating on a general purpose processing platform.

Start date system 402 prompts the user to enter a start date for use in generating compliance data. In one exemplary embodiment, start date system 402 can receive a start date that allows the user to go back a predetermined number of days so as to generate compliance data for prescriptions during a predetermined timeframe of interest to the user. For example, a user may want to generate compliance data in order to make certain that a sales volume meets certain sales volume objectives, and can provide start dates to start date system 402 based on the results of previous start date submittals, based on experience with fall offs or patients who take prescriptions to other pharmacies for filling, or other suitable data.

Compliance revenue calculation system 404 receives compliance data and generates revenue data based on the compliance data. In one exemplary embodiment, compliance revenue calculation system 404 can receive prescription data that identifies the number of days out of compliance a prescription is, the number of dosages that need to be refilled, the profit to be realized from the sale of the prescription refill, the profit to be realized by making the prescription refill in terms of an additional bonus, and other suitable data. Compliance revenue calculation system 404 can rank out of compliance prescriptions, so as to allow an operator to determine the prescriptions having the highest revenue-generating capability.

In operation, system 400 allows compliance data to be compiled and used by a pharmacist or other users to identify persons having prescriptions for pharmaceuticals that have expired and who should order additional medicine, such as to alert such patients of dangerous situations that can result from the failure to take medicines in accordance with the prescribed regime. System 400 further allows revenue to be enhanced using compliance data, to create an incentive to perform compliance-related activities.

FIG. 5 is a diagram of a system 500 for providing persistence data in accordance with an exemplary embodiment of the present invention. System 500 includes persistence system 202, end date system 502 and persistence revenue calculation system 504, each of which can be implemented in hardware, software, or a suitable combination of hardware and software, and which can be one or more software systems operating on a general purpose processing platform.

End date system 502 prompts the user to enter an end date for use in generating persistence data. In one exemplary embodiment, end date system 502 can receive an end date that allows the user to go forward a predetermined number of days so as to generate persistence data for prescriptions during a predetermined timeframe of interest to the user. For example, a user may want to generate persistence data in order to make certain that a sales volume meets certain sales volume objectives, and can provide end dates to end date system 502 based on the results of previous end date submittals, based on experience with advance reminders to certain patients, or other suitable data.

Persistence revenue calculation system 504 receives persistence data and generates revenue data based on the persistence data. In one exemplary embodiment, persistence revenue calculation system 504 can receive prescription data that identifies the number of days until a prescription will need to be refilled, the number of dosages that need to be refilled, the profit to be realized from the sale of the prescription refill, the profit to be realized by making the prescription refill in terms of an additional bonus, and other suitable data. Persistence revenue calculation system 504 can rank the prescriptions, so as to allow an operator to determine the prescriptions having the highest revenue-generating capability.

In operation, system 500 allows persistence data to be compiled and used by a pharmacist or other users to identify persons having prescriptions for pharmaceuticals that will expire in the future and who should be reminded to order additional medicine, such as to alert such patients of dangerous situations that can result from the failure to take medicines in accordance with the prescribed regime. System 500 further allows revenue to be enhanced using persistence data, to create an incentive to perform persistence-related activities.

FIG. 6 is a diagram of a system 600 for generating sales volume data in accordance with an exemplary embodiment of the present invention. System 600 includes data volume system 206 and manufacturer rebate system 602, competing product system 604 and revenue calculation system 606, each of which can be implemented in hardware, software, or a suitable combination of hardware and software, and which can be one or more software systems operating on a general purpose processing platform.

Manufacturing rebate system 602 receives manufacturer rebate data and provides shortfall data based on volume data. In one exemplary embodiment, manufacturer rebate system 602 can receive data from a manufacturer regarding various manufacturer rebates for products, such as a discount to be applied for a number of units sold or based on sales volume data, a rebate to be awarded upon sale of a number of units being sold or based on sales volume data, or other suitable data. Manufacturer rebate system 602 can then track the number of units of a product sold by a pharmacist and can generate notification data advising the pharmacist of the shortfall for additional units that should be sold, the number of units in terms of sales volume that they have exceeded such requirements for, and other suitable data.

Competing product system 604 receives competing product data from a manufacturer or other sources and uses the competing product data to determine the sales volume for a given manufacturer and product. In one exemplary embodiment, competing product system 604 can also store data for products that don't directly compete in terms of having the same active ingredient, but which do compete in terms of usage or effect, such as drugs that have the same effect or reason for being prescribed as that of a reference drug. Competing product system 604 can thus identify competing products that have been sold by a pharmacist that cut into the sales volume for a given pharmaceutical and can generate sales volume data for use in calculating revenue data.

Revenue calculation system 606 receives manufacturer rebate data, prescription data, product sales data and competing product data and generates revenue data. In one exemplary embodiment, revenue calculation system 606 can generate the amount of revenue that a pharmacist has obtained by having a certain sales volume for a pharmaceutical, the amount of revenue that the pharmacist stands to gain by meeting a next sales volume level, the amount of revenue that a pharmacist has lost by selling products that are not in a rebate program, or other suitable data.

In operation, system 600 allows sales volume data to be generated and managed, such as by identifying manufacturers for which sales volume data is relevant, categorizing competing products, calculating revenue and providing feedback to pharmacists so that they can utilize the sales volume data to make decisions on which product to recommend when two or more identical products are available at the same or lower cost to the consumer. For example, the pharmacist may be able to provide a lower cost to the consumer by being able to determine whether a manufacturer's rebate will be received, thus lowering the pharmacist's cost of ingredients.

FIG. 7 is a diagram of a system 700 for providing insurance charge functionality in accordance with an exemplary embodiment in the present invention. System 700 includes insurance charge system 208 and location selection system 702, submitted price system 704, and approved price system 706, each of which can be implemented in hardware, software, or a suitable combination of hardware and software, and which can be one or more software systems operating on a general purpose processing platform.

Location selection system 702 allows a user to select one or more locations for use in developing market price estimates. In one exemplary embodiment, a pharmacist can survey related markets, areas covered by a zip, code, areas in a geographic location such as city or county, or other suitable locations to determine prices for a given pharmaceutical that have been submitted by other pharmacists in those areas, and amounts that were approved for payment by insurance companies. Likewise, location selection system 702 can allow pharmacies within a predetermined distance of a particular doctor, doctors within a predetermined distance of a particular pharmacy, or other suitable locations to be identified and selected.

Submitted price system 704 tracks prices of products that have been submitted by pharmacy systems for payment. In one exemplary embodiment, a pharmacy system can submit a claim for payment of a prescription to an insurance company having a price based on an estimated value of what they paid for the product after adjusting for overhead costs, profit, and other suitable costs. Submitted price system 704 can store pharmacy data, claim data, insurance company data including group number data, plan number data, location data, or other suitable data.

Approved price system 706 tracks approved price data from insurance companies for pharmaceuticals. In one exemplary embodiment, approved price system 706 can store pharmacy data, claim data, the amount approved by an insurance company for the claim, and other suitable data, such as to allow other pharmacists that have submitted higher submitted prices and received higher approved prices to be identified and for other suitable purposes.

In operation, system 700 allows the charges paid for by insurance companies to be monitored and tracked, such as to allow a pharmacist to submit a request for payment based on what other pharmacists in the area based their value on, what insurance companies have approved other claims for, and other suitable data. For example, a first pharmacist may have a special relationship with the manufacturer based on other product sales, product sales from previous periods, or other suitable data. Based on this manufacturer's relationship, the pharmacist may pay a lower price for a given pharmaceutical then would normally be offered, thus making it difficult for the pharmacist to determine what the reasonable and customary market price for the pharmaceutical should be. System 700 allows a pharmacist to determine what prices other pharmacies have been submitting to insurance companies and what those insurance companies have approved, so as to assist the pharmacist in determining what a reasonable cost for the product is.

Figure 8:
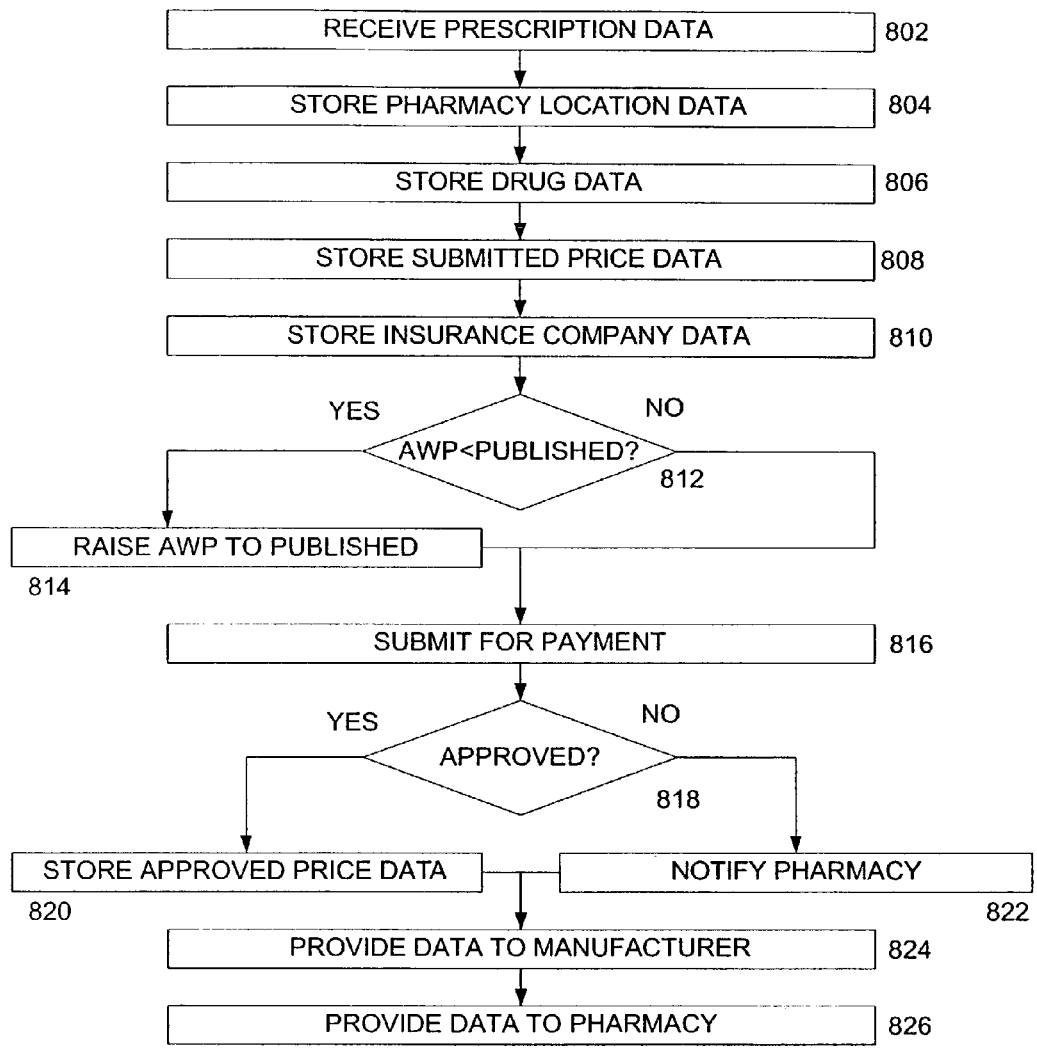
FIG. 8 is a flowchart of a method for managing prescription data in accordance with an exemplary embodiment of the present invention.

FIG. 8 is a flowchart of a method 800 for managing prescription data in accordance with an exemplary embodiment of the present invention. Method 800 allows prescription data to be managed to provide value-added services to pharmacists, manufacturers, and other suitable parties.

Method 800 begins at 802 where prescription data is received. In one exemplary embodiment, the prescription data can be received at switch or other location where it is being processed to obtain approval by an insurance company for payment. The method then proceeds to 804.

At 804, the pharmacy location data is stored. In one exemplary embodiment, pharmacy data location can include a zip code, a street address, map coordinates, or other suitable location data. The method then proceeds to 806.

At 806, the drug data is stored. In one exemplary embodiment, the drug data can include the name of the manufacturer, the name of a medicine or pharmaceutical, a product identification code, the active ingredient of the medicine or pharmaceutical, the dosage, the number of units per package, or other suitable data. The method then proceeds to 808.

At 808, submitted price data is stored. In one exemplary embodiment, the submitted price data can include the price submitted by a pharmacist, such as based on the pharmacist's price list, the average wholesale price, or other suitable data. The method then proceeds to 810.

At 810, insurance company data is stored. The insurance company data can include identification data for the insurance company that must approve the claim, group number data, plan number data, address data, telephone number data, or other suitable data. The method then proceeds to 812.

At 812, it is determined whether the submitted claim price is less than the published average wholesale price. In one exemplary embodiment, a pharmacist can submit a claim for payment having a price that is less than a published average wholesale price, such that the pharmacist is submitting a cost that is lower than that which would normally be approved by an insurance company. If it is determined that the price submitted by the pharmacist is less than the published average wholesale price, the method proceeds to 814 where the price is raised to the published average wholesale price. Otherwise, the method proceeds directly to 816.

At 816, the claim is submitted for payment to an insurance company. In one exemplary embodiment, the claim can be formatted to meet a predetermined format for the insurance company, nonessential data can be removed from the data record, and other suitable processes can be performed. The method then proceeds to 818.

At 818, it is determined whether payment has been approved by the insurance company. If it is determined that payment has been approved, the method proceeds to 820 where the approved price data is stored for later reference. Otherwise, the method proceeds to 822 where the pharmacy is notified that the submitted price has not been approved. In addition, another price can be submitted (such as one based on previously accepted prices), the pharmacy can be prompted to enter the price again, the price approved by the insurance company can be accepted, or other suitable procedures can be used. The method then proceeds from either 820 or 822 to 824.

At 824, prescription processing data is provided to one or more manufacturer systems. In one exemplary embodiment, a manufacturer can purchase data from a switch operator that allows the manufacturer to determine the products being used in a given area, based on location, based on the proximity of the location to a doctor's office, or other suitable functions. For example, a manufacturer can obtain data that shows the sales volume for one of the manufacturer's product in relation to other products, based on pharmacy, pharmacies within a selected distance to a doctor's office, or other suitable data. The method then proceeds to 826.

At 826, data is provided to one or more pharmacy systems. In one exemplary embodiment, a pharmacy can be involved in a sales volume rebate program that provides a rebate to pharmacists based on the sales volume of a given pharmaceutical sold by the pharmacy. The data provided to the pharmacy can include data that allows the pharmacy to determine a number of additional dosages of a given product that need to be sold to reach a sales volume percentage, data that allows the pharmacy to determine prescriptions that are out of compliance, prescriptions that are approaching a refill date, or other suitable data. Likewise, the data can include price data for prescriptions submitted by other pharmacies, approved by insurance companies, or other suitable data.

In operation, method 800 allows prescription data submitted for payment to an insurance company to be tracked and modified so as to provide value-added services to manufacturers, pharmacists, or other suitable parties.

Figure 9:
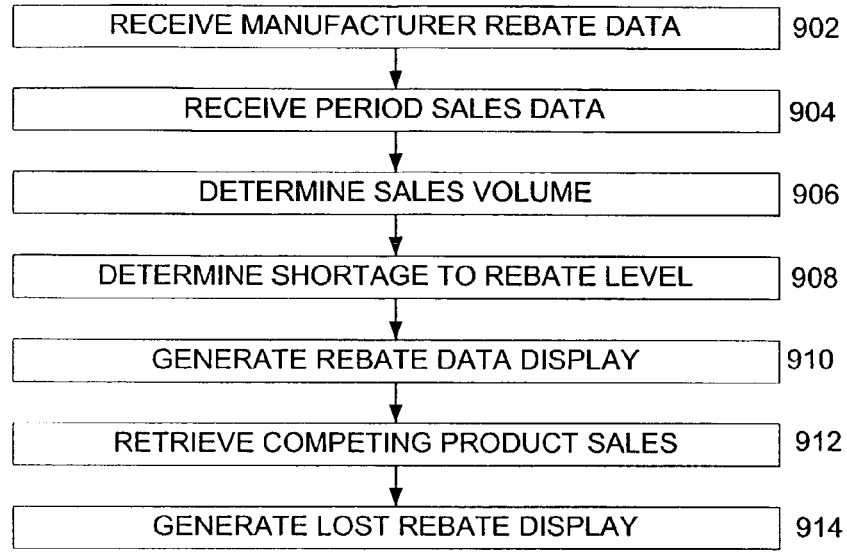
FIG. 9 is a flowchart of a method for a data volume rebate program in accordance with exemplary embodiment of the present invention.

FIG. 9 is a flowchart of a method 900 for a rebate program in accordance with exemplary embodiment of the present invention. Method 900 begins at 902 where manufacturers rebate data is received. In one exemplary embodiment, the manufacturers rebate data can include a volume percentage, rebate data or incentive data based on the number of units of medicine or pharmaceuticals to be dispensed, or other suitable incentive data. The method then proceeds to 904.

At 904, period sales data is received. In one exemplary embodiment, the period sales data can include the number of units of a pharmaceutical that have been sold over a previous period, over a portion of a current period, related pharmaceuticals manufactured by other manufacturers, or other suitable data. The method then proceeds to 906.

At 906, sales volume is determined. In one exemplary embodiment, sales volume is determined by taking the number of units sold for a given pharmaceutical and dividing that by the total number of units sold for all pharmaceuticals in the class, all pharmaceuticals of one or more competing manufacturers, or other suitable data. The method then proceeds to 908.

At 908, shortage to rebate level data is determined. For example, if a rebate can be reached for a sales volume of X % and the current sales volume is Y % where Y<X, then the number of units that need to be sold to reach the X % sales volume level can be determined, based on the number of units already sold. The method then proceeds to 910.

At 910, a rebate data display is generated. In one exemplary embodiment, the rebate data display can include the amount of revenue that can be generated by reaching, rebate levels, inclusive or exclusive of profit from the product, or other suitable data. The method then proceeds to 912.

At 912, competing product dispensed data is retrieved. For example, product sales data for products that have been identified by the manufacturer as directly competing with the prescription can be retrieved, or other suitable data can be retrieved. The method then proceeds to 914.

At 914, a lost rebate display is generated. In one exemplary embodiment, the lost rebate display can show the amount of rebates that the pharmacist lost by dispensing another product based on the failure to meet the rebate volume level or other suitable lost revenue.

In operation, method 900 allows a pharmacist to receive real time feedback on the number of units dispensed that are required in order to meet rebate levels in a volume rebate by unit incentive program, thus decreasing the cost to the patient and increasing the pharmacist's revenue. Method 900 thus allows a pharmacist to determine the number of units that must be dispensed so as to allow them to ask patients if they would have a preference for a specific manufacturer, to obtain compliance or persistence data for previous sales to patients that have used a manufacturer's product, or for other suitable purposes.

Figure 10:
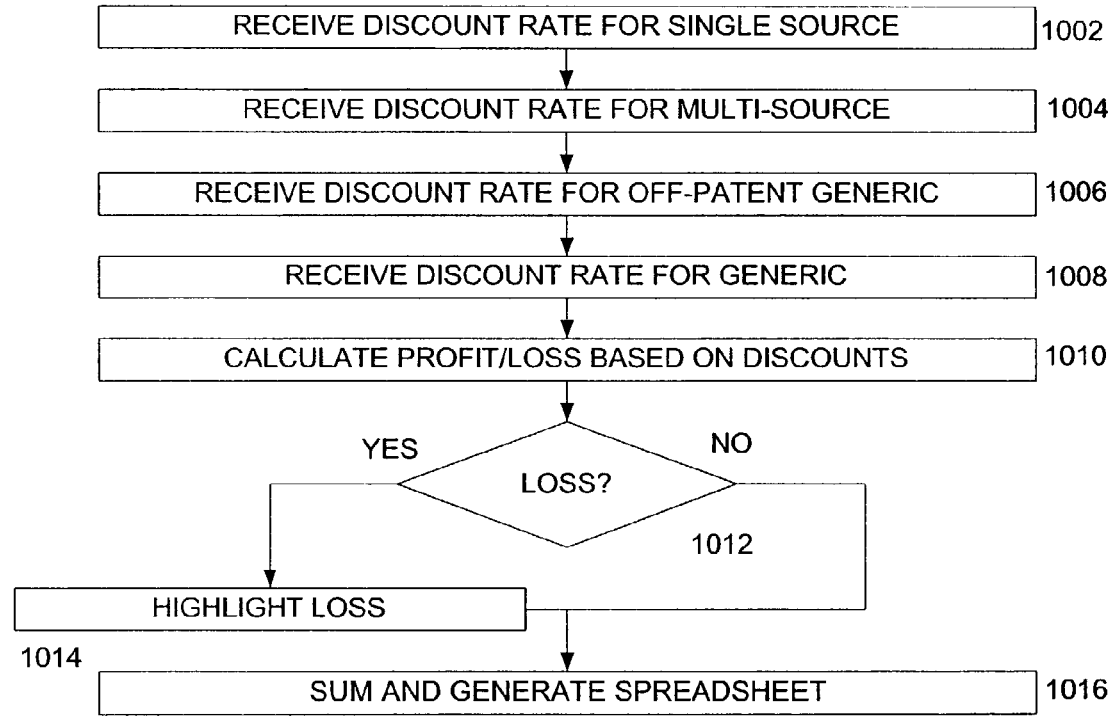
FIG. 10 is a flowchart of a method for generating profit/loss data in accordance with an exemplary embodiment of the present invention.

FIG. 10 is a flowchart of a method 1000 for generating profit/loss data in accordance with an exemplary embodiment of the present invention.

Method 1000 begins at 1002 where a discount rate for a single source pharmaceuticals is received. In one exemplary embodiment, the discount rate is the percentage of the average wholesale price for which a pharmacist typically pays for a pharmaceutical product. The discount rate for single source pharmaceuticals is usually a small fraction of the total product cost. This discount rate reflects the fact that such pharmaceuticals are usually covered by a patent and have been produced following a significant investment in research and development (R&D) expenses, thus requiring the manufacturer to charge higher prices in order to recoup the R&D expenses. The method then proceeds to 1004.

At 1004, a discount rate for a multi-source pharmaceutical is received. The discount rate for a multi-source pharmaceutical is typically higher than the discount rate for a single source pharmaceutical, as the amount of profit that needs to be made from the pharmaceutical to cover R&D expenses incurred to develop the product is less. The method then proceeds to 1006.

At 1006, a discount rate for an off-patent generic product is received. In one exemplary embodiment, when a product goes off patent and can be manufactured as a generic drug, then the number of competing manufacturers may still be relatively small, although some price competition still occurs. For this class of discount rate, the discount rate is typically higher than for a multi-source drug but lower than for a pure generic drug. The method then proceeds to 1008.

At 1008, the discount rate for generic drug is received. Likewise, additional discounts can be received based on manufacturers, types of drugs, locations, or other suitable discount rates. The method then proceeds to 1010.

At 1010, profit and loss is calculated based on discount. For example, the profit or loss for a specific drug will include the average wholesale price, the ingredient cost, the percentage of the discount rate, the ingredient cost paid for by the insurance company, the amount the patient paid, and other fees that were paid, where the difference between all payments and all costs is the indicator of profit and loss. The method then proceeds to 1012.

At 1012 it is determined whether a loss was incurred for each individual prescription sale. If a loss is not incurred, the method then proceeds to 1016. Otherwise, the method proceeds to method 1014 where the loss is highlighted. For example, when a pharmacist sells a pharmaceutical and receives less money from the insurance company and the patient then it cost to provide the pharmaceutical, the pharmacist is losing money on that pharmaceutical product. Thus, the pharmacist should take appropriate steps to increase the amount of money paid by the patient or the insurance company or otherwise increase the revenue or decrease the cost.

At 1014, the products having an associated loss are highlighted to allow such products to be readily identified and the method then proceeds to 1016.

At 1016, the totals for losses and profits are summed and a spreadsheet is generated to display the profit and loss for each unit as well as the overall profit and loss. In this manner, the user can readily determine areas in which drug sales were not profitable, were more profitable, and other areas where optimization could be obtained.

In operation, method 1000 allows a user to readily determine products that are not generating revenue, such as to take corrective actions, increase charges for those products, or otherwise avoid losing money on those products.

FIG. 11 is a flowchart of method 1100 for determining reasonable and customary charges for pharmaceuticals in accordance with an exemplary embodiment of the present invention.

Method 1100 begins at 1102 where drug identification data is received. In one exemplary embodiment, the drug identification data can be received as part of a pharmaceutical or prescription processing. The method then proceeds to 1104.

At 1104, pharmacy location data is received. In one exemplary embodiment, the pharmacy location data can be entered by a pharmacist, can be extracted from a prescription data set, can be provided by a software system that is used by personnel at the pharmacy, or other suitable processes can be used. The method then proceeds to 1106.

At 1106, insurance company data is received. In one exemplary embodiment, a pharmacist can enter the insurance company data, the insurance company data can be extracted from the prescription data, or other suitable processes can be used. The method then proceeds to 1108.

At 1108, submitted price data is retrieved. The submitted price data can include some other price data from one or more other pharmacists in a given geographical area, given demographic area (such as number of persons living in a city) or other suitable price data. The method then proceeds to 1110.

At 1110, the approved price data is retrieved. The approved price data can include approved amounts from an insurance company or other suitable data. The method then proceeds to 1112.

At 1112, the local submitted and approved price data is retrieved. For example, the local submitted and approved price data can be tracked over time, can be used for a given submission, or other suitable data can be used. The method then proceeds to 1114.

At 1114, it is determined whether there is a difference between the local submitted and approved price data and the submitted and approved price data for other pharmacists in the vicinity of the referenced pharmacy or in other suitable comparable demographic locations. If there is no difference, the method proceeds to 1118. Otherwise, the method proceeds to 1116 and a revenue difference is calculated. In one exemplary embodiment, the revenue difference can include the amount of additional money that could have been obtained if the pharmacist had submitted the higher price, can include the amount of money that will be obtained such as where the pharmacist submits the data and the switch operator obtains a percentage of any additional funds obtained through the use of this data, or other suitable revenue differences. The method then proceeds to 1118.

At 1118, results are displayed. In one exemplary embodiment, the results can be displayed to a pharmacist that is making a decision on what to submit a customary and reasonable cost, the results can be displayed in a monthly report format such as showing the amounts of money that were made or the amount of revenue increased through this system, or other suitable results.

In operation, method 1100 allows reasonable and customary expenses or charge submissions for pharmaceuticals from other pharmacies in a location or a similar demographic area to be used to generic submitted and approved price data. Likewise, the results can be used to approach not insurance companies that do not approve submitted prices, or for other suitable purposes.

FIG. 12 is a diagram of a system 1200 for detecting pathogens that have been released into a population based on changes in pharmaceutical use levels in accordance with an exemplary embodiment of the present invention. System 1200 includes pathogen detection system 218 and treatment classification system 1202, treatment analysis system 1204, treatment monitoring system 1206, and inventory monitoring system 1208, each of which can be implemented in hardware, software, or a suitable combination of hardware and software, and which can be one or more software systems operating on a suitable processing platform.

Treatment classification system 1202 receives pathogen group data and associated pharmaceutical data for each pathogen group. In one exemplary embodiment, pathogens can be grouped according to type (e.g. virus type, chemical type, radioactive biological effect type), and pharmaceuticals that may be prescribed to treat the symptoms occurring from exposure to each group of pathogens can be associated with each pathogen group. Likewise, individual pathogens can also be identified, such as pathogens that are known to be the subject of biological warfare programs or that are more likely to be used to inflict casualties on a civilian population (e.g. smallpox virus, plague bacilli), chemical agents (e.g. nerve agents or toxins), radioactive contaminants (e.g. plutonium, cesium), or other individual pathogens.

Treatment analysis system 1204 receives pharmaceutical data and generates treatment statistical data for detecting variations in pharmaceutical prescriptions that exceed normal variations. In one exemplary embodiment, treatment analysis system 1204 can determine weekly, monthly, seasonal, or other variations, can receive data pertaining to advertising campaigns or other factors that may account for an increase in prescribing a pharmaceutical in an area that is greater than would be expected based on statistics, or can otherwise analyze such prescription data to determine normal variations, detect prescription levels that exceed normal variations, and compensate for factors that can be used to account for such excursions over normal so as to reduce the risk of generating a false indication of concern.

Treatment monitoring system 1206 receives treatment data, such as pharmaceutical prescription data, over-the-counter drug data, or other suitable data and compares the treatment data to data ranges generated by treatment analysis system 1204 so as to generate notification data when the level of prescription for such drugs indicates the potential exposure of a population to a pathogen. In one exemplary embodiment, treatment monitoring system 1206 can periodically analyze prescriptions for one or more pharmaceuticals based on an associated pathogen group, an associated geographic group, or other suitable groups, so as to detect indications that a population may have been exposed to a pathogen, as well as to detect the potential pathogen or group of pathogens. In this manner, authorities can be provided with notification data to allow the exposed population to be properly treated for exposure to the pathogen as soon as possible.

Inventory monitoring system 1208 receives pharmacy inventory data and generates inventory statistical data for detecting variations in pharmaceutical inventory that exceed normal variations. In one exemplary embodiment, inventory monitoring system 1208 can determine weekly, monthly, seasonal, or other variations, or can otherwise analyze such inventory data to determine normal variations, detect inventory levels that exceed normal variations, and compensate for factors that can be used to account for such excursions over normal so as to reduce the risk of generating a false indication of concern.

In operation system 1200 allows pathogen exposure of a population to be detected early by monitoring pharmaceuticals that have been prescribed to the population or that are otherwise being used by the population. System 1200 determines normal variations for such pharmaceuticals and monitors prescription data, advertising and marketing data, and other suitable data that can be used to detect when an anomalous variation occurs.

Figure 13:
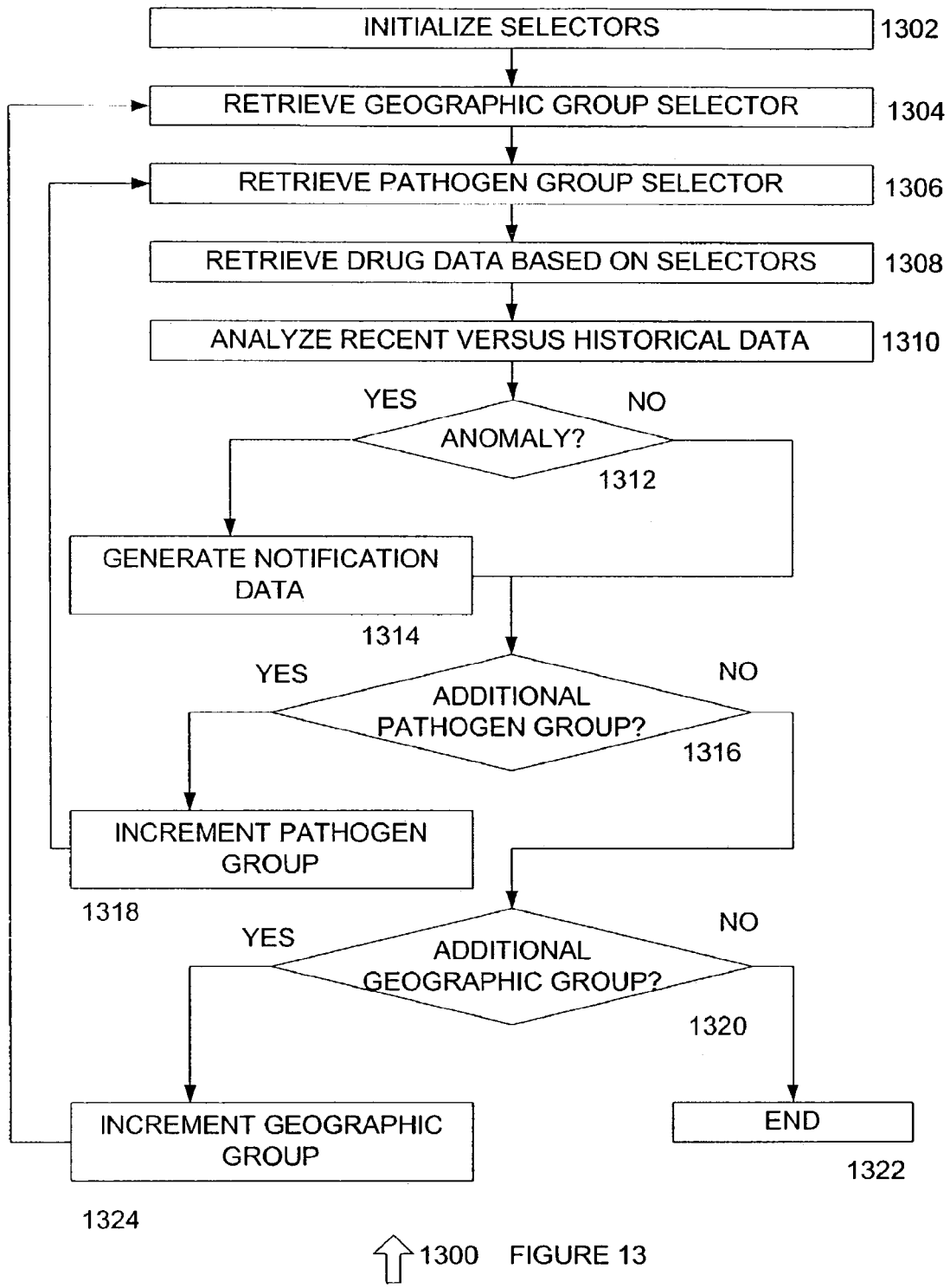
FIG. 13 is a diagram of a method for monitoring for signs of pathogens that have been released into a population in accordance with an exemplary embodiment of the present invention.

FIG. 13 is a diagram of a method 1300 for monitoring for signs of pathogens that have been released into a population in accordance with an exemplary embodiment of the present invention. Method 1300 begins at 1302, where selectors are initialized. In one exemplary embodiment, the selectors can include a geographic group selector that is used to identify prescription data and other pharmaceutical data from a geographic group, a pathogen group selector that is used to select pharmaceuticals that could be used to treat a particular pathogen or group of pathogens, and other suitable selector data. The method then proceeds to 1304.

At 1304, the geographic group selector is retrieved. In one exemplary embodiment, geographic selectors can be stored in an array or other data formats, and the current geographic selector is retrieved for use in selecting other data fields that are correlated to the geographic selector. The method then proceeds to 1306.

At 1306, the pathogen group selector is retrieved. In one exemplary embodiment, pathogen selectors can be stored in an array or other data formats, and the current pathogen selector is retrieved for use in selecting other data fields that are correlated to the pathogen selector. The method then proceeds to 1308.

At 1308, drug or pharmaceutical data is retrieved based on the geographic group and the pathogen group. In one exemplary embodiment, each dispensed pharmaceutical can have associated geographic data and associated pathogen data, such that dispensed pharmaceuticals matching the geographic data and pathogen data can be selected. In another exemplary embodiment, the pathogen selectors can include a list of predetermined pharmaceuticals, such that each incidence in which one of the predetermined pharmaceuticals was dispensed in the associated geographic area is retrieved. Likewise, other suitable processes can be used, such as obtaining inventory data for pharmaceuticals. The method then proceeds to 1310.

At 1310, pharmaceutical data for a recent period, such as the previous day or week, is analyzed versus historical data. In one exemplary embodiment, the total number of pharmaceuticals dispensed, the number of patients receiving pharmaceuticals, the number of pharmaceuticals dispensed having a certain dose, or other suitable data can be analyzed to determine whether that number exceeds historical variations, which can be adjusted for seasonal variations, variations due to known local conditions or marketing campaigns, or other suitable data. The method then proceeds to 1312.

At 1312, it is determined whether an anomaly was noted in the analysis. In one exemplary embodiment, an anomaly can include an unexpected decrease or increase in the number of pharmaceuticals dispensed or persons receiving the pharmaceuticals or other suitable data. For example, the number of persons receiving certain pharmaceuticals might decrease in the event of exposure of a population to a pathogen if that pathogen removes such persons from the population (such as by death or relocation to a hospital), might increase if the exposure causes the person to receive the pharmaceutical, or other anomalies can occur. If it is determined that no anomaly is present, the method proceeds to 1316. Otherwise, the method proceeds to 1312 where notification data is generated, and the method then proceeds to 1316.

At 1316, it is determined whether an additional pathogen group exists in the geographical group. If no additional pathogen group exists, the method proceeds to 1320. Otherwise, the method proceeds to 1318 where the pathogen group is incremented. The method then returns to 1306.

At 1320, it is determined whether an additional geographic group requires analysis. If no additional geographic group exists, the method proceeds to 1322 and terminates. Otherwise, the method proceeds to 1324 where the geographic group is incremented. The method then returns to 1304.

In operation, method 1300 allows pharmaceutical data to be analyzed to detect indications of the release of pathogens into a population. Method 1300 analyzes recent pharmaceutical use based on historical data to identify variations in such use that exceed normal variations.

Although exemplary embodiments of a system and method of the present invention have been described in detail herein, those skilled in the art will also recognize that various substitutions and modifications can be made to the systems and methods without departing from the scope and spirit of the appended claims.

What is claimed is:

1. A prescription data management system comprising:
  a switch system embodied on a non-transitory computer readable storage medium, the switch system configured to:
    receive volume rebate program data from a manufacturer system, the volume rebate program data identifying a benefit provided in response to a volume of sales of a prescription item by a pharmacy in proportion to a volume of sales of one or more competing prescription items by the pharmacy;
    receive prescription data generated by the pharmacy, the prescription data identifying:
      at least one prescription for the prescription item submitted by the pharmacy; and
      at least one prescription for the one or more competing prescription items submitted by the pharmacy, the one or more competing prescription items competing with the prescription item;
  a sales volume system embodied on a non-transitory computer-readable storage medium, the sales volume system configured to interface with the switch system and to generate sales volume data from at least a portion of the prescription data, the sales volume data representing a volume of the prescription item sold by the pharmacy in relation to a volume of the one or more competing prescription items sold by the pharmacy; and
  a rebate system embodied on a non-transitory computer-readable storage medium, the rebate system configured to interface with the sales volume system and to:
    generate incentive target reward data using at least a portion of the volume rebate program data and at least a portion of the sales volume data; and provide the incentive target reward data to the pharmacy, said incentive target reward data representing or from which can be determined additional sales by the pharmacy of the prescription item required for the pharmacy to receive the benefit.

2. The system of claim 1 further comprising a persistence system configured to interface with the switch system and to generate future prescription refill data from at least a portion of the prescription data.

3. The system of claim 1 further comprising a compliance system configured to interface with the switch system and to generate past due prescription refill data from at least a portion of the prescription data.

4. The system of claim 1 further comprising an insurance charge system configured to interface with the switch system and to generate approved charge data from at least a portion of the prescription data.

5. The system of claim 1 further comprising a manufacturer charge system configured to interface with the switch system and to generate per-unit charge data from at least a portion of the prescription data.

6. The system of claim 1 further comprising a pharmacy charge system configured to interface with the switch system and to generate percentage fee data from at least a portion of the prescription data.

7. The system of claim 1 further comprising a prescription data system configured to interface with the switch system and to receive fill date data and number of dosages data and to generate compliance data or persistence data.

8. The prescription data management system of claim 1, further comprising a monitoring system configured to detect anomalous variations in the prescription data.

9. The prescription data management system of claim 8, wherein the monitoring system detects geographic incidence of pathogen or contamination introduction into a population.

10. A method for prescription data management, the method comprising:

receiving, by a switch system operating on a hardware server platform:

volume rebate program data from a manufacturer system, the volume rebate program data identifying a benefit provided in response to a volume of sales of a prescription item by a pharmacy in proportion to a volume of sales of one or more competing prescription items by the pharmacy; and prescription data generated by a pharmacy, the prescription data identifying:

at least prescription for the prescription item submitted by the pharmacy; and at least one prescription for the one or more competing prescription items submitted by the pharmacy, the one or more competing prescription items competing with the prescription item;

generating, by a sales volume system operating on a hardware server platform and configured to interface with the switch system, sales volume data from at least a portion of the prescription data, the sales volume data representing a volume of the prescription item sold by the pharmacy in relation to a volume of the one or more competing prescription items sold by the pharmacy;

generating, by a rebate system operating on a hardware server platform and configured to interface with the sales volume system, incentive target reward data using at least a portion of the volume rebate program data and at least a portion of the sales volume data, wherein the incentive target reward data provides an indication of additional sales by the pharmacy of the prescription item which are required for the pharmacy to receive the benefit; and providing, by the rebate system, the incentive target reward data to the pharmacy.

11. The method of claim 10 further comprising:
generating future prescription refill data from at least a portion of the prescription data.

12. The method of claim 10 further comprising:
generating past due prescription refill data from at least a portion of the prescription data.

13. The method of claim 10 further comprising:
generating approved charge data from at least a portion of the prescription data.

14. The method of claim 10 further comprising:
generating per-unit charge data from at least a portion of the prescription data.

15. The method of claim 10 further comprising:
generating percentage fee data from at least a portion of the prescription data.

16. The method of claim 10 further comprising:
receiving fill date data and number of dosages data.

17. The method of claim 16 further comprising:
generating compliance data.

18. The method of claim 16 further comprising:
generating persistence data.

19. The method of claim 10, further comprising detecting geographic incidence of pathogen or contamination introduction into a population.

20. The method of claim 10, further comprising monitoring anomalous variations in the prescription data.

* * * * *